US010457630B2

(12) United States Patent
Cabon et al.

(10) Patent No.: US 10,457,630 B2
(45) Date of Patent: Oct. 29, 2019

(54) RECLAMATION OF NOBLE PRODUCTS IN A METHOD FOR PRODUCING (METH)ACRYLIC ESTER

(71) Applicant: Arkema France, Colombes (FR)

(72) Inventors: Yves Cabon, Metz (FR); Fanny Dubut, Metz (FR); Benoit Riflade, Bazas (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/546,074

(22) PCT Filed: Jan. 28, 2016

(86) PCT No.: PCT/FR2016/050177
§ 371 (c)(1),
(2) Date: Jul. 25, 2017

(87) PCT Pub. No.: WO2016/124837
PCT Pub. Date: Aug. 11, 2016

(65) Prior Publication Data
US 2018/0009736 A1    Jan. 11, 2018

(30) Foreign Application Priority Data

Feb. 4, 2015 (FR) ...................... 15 50844

(51) Int. Cl.
| | |
|---|---|
| *C07C 213/06* | (2006.01) |
| *C07C 67/03* | (2006.01) |
| *C07C 213/10* | (2006.01) |
| *C07C 67/327* | (2006.01) |
| *C07C 67/54* | (2006.01) |
| *C07C 219/08* | (2006.01) |

(Continued)

(52) U.S. Cl.
CPC ............ *C07C 213/06* (2013.01); *C07C 67/03* (2013.01); *C07C 67/327* (2013.01); *C07C 67/54* (2013.01); *C07C 213/10* (2013.01); *C07C 219/08* (2013.01); *B01D 3/143* (2013.01); *C08F 20/18* (2013.01)

(58) Field of Classification Search
CPC ... C07C 213/06; C07C 213/10; C07C 219/08; C07C 67/03; C07C 67/327; C07C 67/54; B01D 3/143; C08F 20/18; Y02P 20/51; Y02P 20/582
USPC .......................................................... 560/218
See application file for complete search history.

(56) References Cited

U.S. PATENT DOCUMENTS

| 5,534,652 A * | 7/1996 | Jones .................. C07C 67/08 560/98 |
| 2004/0171868 A1* | 9/2004 | Geisendoerfer ........ C07C 67/54 560/217 |
| 2014/0350291 A1* | 11/2014 | Paul ...................... C07C 67/327 560/172 |

FOREIGN PATENT DOCUMENTS

JP        2005015398 A2    1/2005

* cited by examiner

*Primary Examiner* — Deborah D Carr
(74) *Attorney, Agent, or Firm* — Lynn B. Morreale

(57) ABSTRACT

The invention relates to a method for producing a (meth) acrylic ester with improved productivity, by transesterfication of a light alkyl (meth)acrylate with a heavy alcohol. The method of the invention includes the recycling of noble products recovered after the thermal treatment of heavy fractions generated during the synthesis, said thermal treatment being carried out in the presence of a dialkyl phthalate, the alkyl chain of which corresponds to that of the light alkyl (meth)acrylate. The invention applies to the production of N,N-dimethyaminoethyl acrylate from ethyl acrylate.

15 Claims, 1 Drawing Sheet

(51) Int. Cl.
*B01D 3/14* (2006.01)
*C08F 20/18* (2006.01)

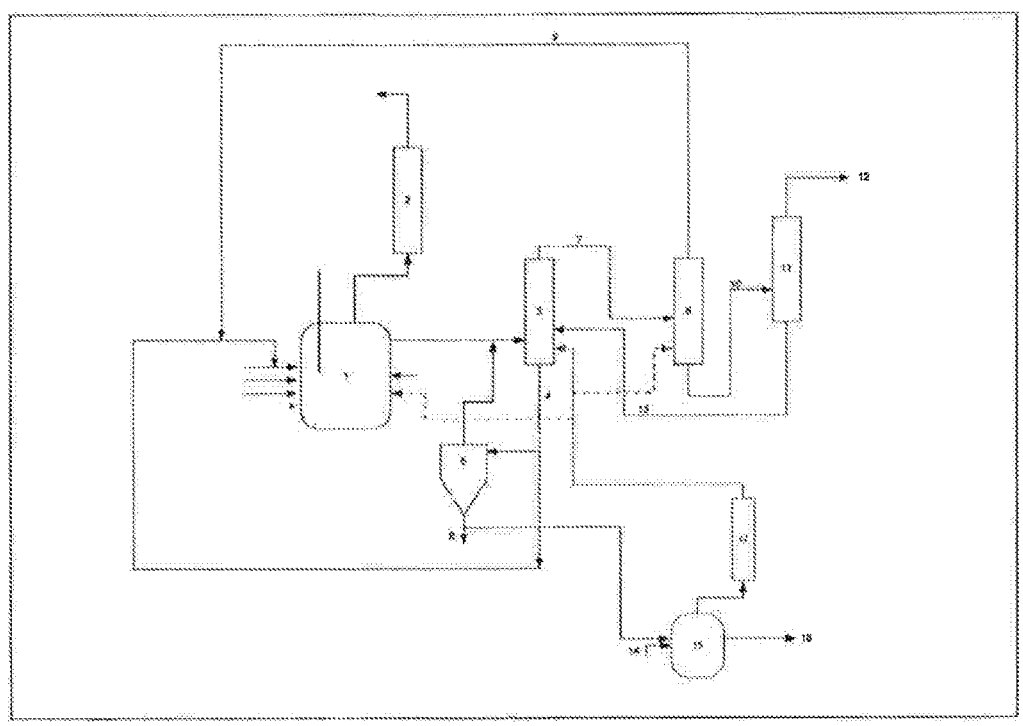

RECLAMATION OF NOBLE PRODUCTS IN A METHOD FOR PRODUCING (METH)ACRYLIC ESTER

CROSS-REFERENCE TO RELATED APPLICATIONS

This application is a national stage application under 35 U.S.C. § 371 of PCT/FR2016/050177, filed Jan. 28, 2016 which claims benefit to application FR15.50844, filed Feb. 4, 2015.

TECHNICAL FIELD

The present invention relates to the production of (meth) acrylic ester according to a continuous transesterification process, and in particular the production of N,N-dimethylaminoethyl acrylate (hereinafter denoted ADAME).

The invention provides a process for producing a (meth) acrylic ester with improved productivity, by transesterification of a light alkyl (meth)acrylate with a heavy alcohol. The process of the invention includes the recycling of the valuable products recovered after heat treatment of heavy fractions generated during synthesis, said heat treatment being carried out in the presence of a dialkyl phthalate, the alkyl chain of which corresponds to that of the light alkyl (meth) acrylate.

PRIOR ART AND TECHNICAL PROBLEM

The economic viability of industrial processes for producing (meth)acrylic derivatives is strongly linked to the recycling of fractions generated during the process for purification of the crude products, these fractions being liable to contain unreacted reagents, reclaimable by-products and/or the desired compound, in not inconsiderable amounts, and also the reaction catalyst.

Transesterification processes involve a "short" chain, $C_1$-$C_4$, alkyl (meth)acrylate, referred to as light alkyl (meth) acrylate or light (meth)acrylate, which reacts with an alcohol with a "longer" carbon-based chain, referred to as heavy alcohol, generally in the presence of a catalyst and of polymerization inhibitors, according to the following general formula (1):

$$H_2C=C(R)COOR_1 + R_2OH \leftrightarrows H_2C=C(R)COOR_2 + R_1OH \quad (1)$$

with R=H or $CH_3$; $R_1$=$C_1$-$C_4$ alkyl chain; $R_2OH$=heavy alcohol

In order to shift the equilibrium towards the formation of "long" chain alkyl (meth)acrylate, the light alcohol $R_1OH$ released during the reaction is continuously eliminated in the form of an azeotrope with the light (meth)acrylate. Due to the presence of light alcohol, this azeotrope is advantageously recycled to the unit for producing light (meth) acrylate, the synthesis of which is based on the direct esterification of (meth)acrylic acid with the light alcohol.

The transesterification reaction of (meth)acrylic derivatives leads to the formation of impurities, such as Michael adducts resulting from Michael addition reactions of an alcohol molecule (containing a labile hydrogen atom) onto the double bond of the (meth)acrylic ester.

For example, in the case of the production of ADAME by transesterification between a light acrylate, such as methyl acrylate (MA) or ethyl acrylate (EA), and N,N-dimethylaminoethanol (DMAE), the as yet unreacted alcohol or the light alcohols generated during the reaction (methanol or ethanol) are added at the double bond of the already formed ADAME or of the unreacted light acrylate (MA or EA), to form heavy Michael addition by-products [DMAE+ADAME] of formula:

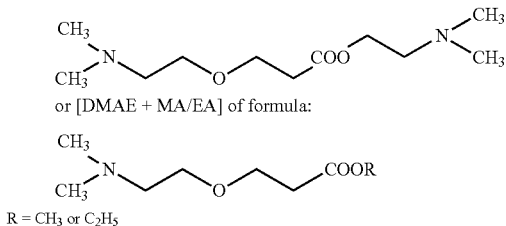

or [DMAE + MA/EA] of formula:

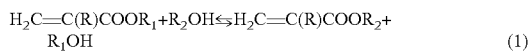

R = $CH_3$ or $C_2H_5$

A characteristic of these heavy by-products is that their boiling point is above the boiling points of the products used in the reaction and of the desired ADAME.

These heavy by-products are generally concentrated in a "heavy fraction", separated during the process for purifying the crude ADAME, this heavy fraction possibly comprising, within the context of the present invention, not only Michael adducts but also, generally, the transesterification catalyst, the polymerization inhibitors which were added to the reaction, and also a minor fraction of residual reagents and/or of ADAME.

The elimination of this heavy fraction generally poses a problem since it must be incinerated, and leads to significant losses of raw materials (especially DMAE) and of finished product (ADAME) which are present in this fraction in free form or in the form of Michael adducts.

The residual reagents and/or the ADAME present in the heavy fraction are valuable products since recycling thereof makes it possible to directly increase the productivity of the process. Recycling all of the heavy fraction cannot be envisaged in a continuous industrial process because it would lead to an accumulation of Michael adducts in the purification loop unless the Michael adducts were thermally cracked beforehand to give their constituent components.

To this end, patent application WO 2013/045786, in the applicant's name, proposed carrying out thermal cracking of the heavy (meth)acrylic fractions generated during the production of (meth)acrylic esters by transesterification, to recover the valuable products in the form of a stream of recyclable distillate. This process is especially characterized by the introduction of at least one antifouling agent and optionally a viscosity-reducing agent (or fluxing agent) into the heavy fractions, in order to carry out thermal cracking so as to avoid fouling the apparatus used and obtain a final residue that is sufficiently fluid to be transported by means of a pump and eliminated by incineration.

However, the applicant has observed that the presence of an antifouling compound such as a phosphoric ester, or of a compound fulfilling the role both of antifouling agent and fluxing agent, such as the product sold by Nalco under the name Nalco® EC3368A, leads to the formation of impurities in the distillate generated during the thermal cracking.

In particular, the presence of a not inconsiderable amount of methanol has been observed in the abovementioned process for synthesising ADAME from EA using the Nalco® EC 3368A product as fluxing agent. The presence of methanol is particularly bothersome because the methanol is found in the various recycling loops, thereby polluting, upstream in the reaction, the azeotrope which is used to at least partially synthesize the ethyl acrylate, and consequently polluting the ethyl acrylate.

Surprisingly, the inventors have now discovered that the use of a dialkyl phthalate, the alkyl chain of which corresponds to that of the light alkyl (meth)acrylate, for carrying out the thermal cracking of heavy fractions generated during the production of (meth)acrylic esters by transesterification of a light alkyl (meth)acrylate with a heavy alcohol, not only makes it possible to avoid fouling of the apparatus used and to obtain a final residue which is transportable by means of a pump in order to be incinerated, but also avoids the potential pollution risks. This use thus expands the possibilities for recycling valuable, reclaimable products. In addition, unexpectedly, it has been possible to demonstrate that such a compound has a beneficial effect on the effectiveness of the thermal cracking.

One of the aims of the present invention is thus to overcome the drawbacks of the abovementioned process described in document WO 2013/045786. The present invention makes it possible to recycle, at different stages of the purification section, valuable products (starting compounds or finished product) which can be potentially recovered from the heavy fraction generated in a process for synthesizing (meth)acrylic esters by transesterification of a light alkyl (meth)acrylate, in particular in a process for synthesizing dialkylaminoalkyl (meth)acrylate. This enhancement leads to improving the material balance of the process and reducing the final amounts of residue to be incinerated, and it consequently represents an economic advantage.

It has moreover become apparent to the inventors that the present invention could also be applied to the production of alkyl (meth)acrylate with a linear or branched alkyl chain comprising from 5 to 12 carbon atoms.

SUMMARY OF THE INVENTION

Therefore, a subject of the present invention is a process for recovering valuable products from a heavy (meth)acrylic fraction generated during production of a (meth)acrylic ester by transesterification reaction of a light $C_1$-$C_4$ alkyl (meth)acrylate with a heavy alcohol in the presence of a catalyst, the heavy fraction comprising at least valuable products and Michael adducts resulting from addition reactions on the (meth)acrylic double bonds and also the catalyst, said process comprising the heat treatment of said heavy fraction at a temperature sufficient to crack the Michael adducts into their constituent valuable components, the recovery of the valuable products in the form of a distillate and the elimination of the fluid final residue by means of a pump, characterized in that the heat treatment is carried out in the presence of at least one dialkyl phthalate, the alkyl chain of which corresponds to that of the light alkyl (meth)acrylate.

According to one embodiment of the invention, at least a portion of the heavy fraction is recycled to the transesterification reaction, the other portion being subjected to said heat treatment.

According to one embodiment of the invention, the heavy fraction is subjected beforehand to purification by passage over a film evaporator, at least a portion of the bottom stream from the film evaporator being recycled to the transesterification reaction, the other portion being subjected to said heat treatment. The light compounds present in the top stream from the film evaporator may thus advantageously be recycled.

The heavy fraction contains a significant amount of catalyst, possibly representing up to 50% by weight. Recycling of the still active catalyst to the transesterification reaction, via the recycling of at least a portion of the heavy fraction, makes it possible to significantly reduce the feed of fresh catalyst into the reactor.

The term "(meth)acrylic" means acrylic or methacrylic; the term "(meth)acrylate" means acrylate or methacrylate.

Valuable products is intended to mean unreacted reagents (heavy alcohol and light (meth)acrylate used in the transesterification reaction) and the desired (meth)acrylic ester.

Heavy alcohol is intended to mean a primary or secondary alcohol comprising a linear or branched alkyl chain ranging from 4 to 18 carbon atoms, possibly being interrupted by one or more heteroatoms such as N or O.

The heavy fraction comprises Michael adducts and valuable products, but also generally the transesterification catalyst and the polymerization inhibitors which have been added to the reaction.

According to the invention, the addition of at least one dialkyl phthalate into the heavy fraction makes it possible to obtain an improved degree of thermal cracking, and minimizes the residual amount of Michael adduct in the final residue.

According to the invention, associating the nature of the dialkyl phthalate, introduced as antifouling/fluxing agent in the step of cracking of the Michael adducts, to the nature of the light alkyl (meth)acrylate used as starting material in the process, avoids the generation of impurities which are damaging for the recycling of the valuable products.

According to one embodiment of the invention, the heavy alcohol is an aminoalcohol of formula (II):

$$HO-A-N(R'_2)(R'_3) \qquad (II)$$

in which

A is a linear or branched $C_1$-$C_5$ alkylene radical, $R'_2$ and $R'_3$, which are identical to or different from one another, each represent a $C_1$-$C_4$ alkyl radical.

The heavy alcohol may for example be N,N-dimethylaminoethanol (DMAE), N,N-diethylaminoethanol, or N,N-dimethylaminopropanol.

According to a preferred embodiment of the invention, the aminoalcohol is N,N-dimethylaminoethanol (DMAE), and the (meth)acrylic ester is N,N-dimethylaminoethyl acrylate (ADAME).

According to one embodiment of the invention, the heavy alcohol is an alcohol of formula $R_2OH$, in which $R_2$ represents a linear or branched $C_5$-$C_{12}$ alkyl chain. The heavy alcohol may be primary or secondary. The heavy alcohol is, for example, 2-ethylhexanol or 2-octanol.

According to a preferred embodiment of the invention, the light alkyl (meth)acrylate is methyl acrylate and the dialkyl phthalate is dimethyl phthalate.

According to a preferred embodiment of the invention, the light alkyl (meth)acrylate is ethyl acrylate and the dialkyl phthalate is diethyl phthalate.

According to a preferred embodiment of the invention, the light alkyl (meth)acrylate is butyl acrylate and the dialkyl phthalate is dibutyl phthalate.

A second subject of the invention is a process for producing a (meth)acrylic ester by transesterification reaction between a light $C_1$-$C_4$ alkyl (meth)acrylate and a heavy alcohol, said process comprising at least the following steps:
a) subjecting a reaction mixture, comprising a light alkyl (meth)acrylate, a heavy alcohol, a transesterification catalyst and at least one polymerization inhibitor, to transesterification conditions in order to form i) a mixture of products comprising the (meth)acrylic ester and the unreacted light alkyl (meth)acrylate and heavy alcohol, the catalyst, the polymerization inhibitors, Michael adducts resulting from addition reactions onto the (meth)acrylic double bonds, and other heavy compounds such as oligomers or polymers; and ii) an azeotropic mixture of light alkyl (meth)acrylate/free light alcohol;

b) distilling the mixture i) of products in order to recover, at the top, a stream composed essentially of the desired (meth)acrylic ester and light products, comprising a minority fraction of Michael adducts, heavy products and polymerization inhibitors, but free or substantially free of catalyst, and in order to leave, at the bottom, a heavy fraction comprising catalyst, polymerization inhibitors, Michael adducts and heavy compounds, with a minority fraction of the desired (meth)acrylic ester and heavy alcohol and traces of light products;

c) purifying the top stream, making it possible to obtain the purified (meth)acrylic ester;

d) subjecting at least a portion of the heavy fraction to a process for recovering the valuable products in the form of a distillate as defined above;

e) recycling at least a portion of said distillate into at least one step chosen from step a) of reaction, step b) of distillation and step c) of purification;

f) optionally recycling the azeotropic mixture ii) formed in step a), to the light alkyl (meth)acrylate production unit;

g) optionally recycling at least a portion of the fluid final residue resulting from step d), to step a) of reaction;

h) incinerating the fluid final residue resulting from step d);

i) optionally recycling a portion of the heavy fraction to step a) of reaction.

According to one embodiment of the invention, the step of purification c) is carried out by means of two distillation columns in series and at least a portion of the distillate resulting from step d) is recycled to the top of the first purification column.

According to one embodiment of the invention, the heavy fraction is at least partially subjected beforehand to purification by passage over a film evaporator before step d).

According to one embodiment, a portion of the bottom stream from the film evaporator is recycled to step a) of reaction.

The invention is advantageously carried out for the production of N,N-dimethylaminoethyl (ADAME) by the transesterification reaction between ethyl acrylate (EA) and N,N-dimethylaminoethanol (DMAE), step d) being carried out in the presence of diethyl phthalate.

The invention is now described in more detail and non-limitingly in the following description, with reference to the appended FIG. 1 which schematically represents different embodiments according to the invention in a facility for a continuous process for producing ADAME by transesterification starting from EA and DMAE.

DETAILED DESCRIPTION OF THE INVENTION

In the process according to the invention, the heat treatment of the heavy fraction is carried out in the presence of at least one $C_1$-$C_4$ dialkyl phthalate, and the alkyl chain is similar to the alkyl chain of the light alkyl (meth)acrylate used as starting material for producing the (meth)acrylic ester.

According to one embodiment of the invention, the light alkyl (meth)acrylate is ethyl acrylate (EA), the heavy alcohol is N,N-dimethylaminoethanol (DMAE), the (meth)acrylic ester is N,N-dimethylaminoethyl acrylate (ADAME), and the dialkyl phthalate is diethyl phthalate.

According to one embodiment of the invention, the light alkyl (meth)acrylate is methyl acrylate (MA), the heavy alcohol is N,N-dimethylaminoethanol (DMAE), the (meth)acrylic ester is N,N-dimethylaminoethyl acrylate (ADAME), and the dialkyl phthalate is dimethyl phthalate.

According to one embodiment of the invention, the light alkyl (meth)acrylate is butyl acrylate (BuA), the heavy alcohol is N,N-dimethylaminoethanol (DMAE), the (meth)acrylic ester is N,N-dimethylaminoethyl acrylate (ADAME), and the dialkyl phthalate is dibutyl phthalate.

According to one embodiment of the invention, the light alkyl (meth)acrylate is methyl acrylate (MA), the heavy alcohol is 2-ethylhexanol, the (meth)acrylic ester is 2-ethylhexyl acrylate (2EHA), and the dialkyl phthalate is dimethyl phthalate.

According to one embodiment of the invention, the light alkyl (meth)acrylate is ethyl acrylate (EA), the heavy alcohol is 2-ethylhexanol, the (meth)acrylic ester is 2-ethylhexyl acrylate (2EHA), and the dialkyl phthalate is diethyl phthalate.

According to one embodiment of the invention, the light alkyl (meth)acrylate is butyl acrylate (BuA), the heavy alcohol is 2-ethylhexanol, the (meth)acrylic ester is 2-ethylhexyl acrylate (2EHA), and the dialkyl phthalate is dibutyl phthalate.

According to one embodiment of the invention, the light alkyl (meth)acrylate is methyl acrylate (MA), the heavy alcohol is 2-octanol, the (meth)acrylic ester is 2-octyl acrylate (2OCTA), and the dialkyl phthalate is dimethyl phthalate.

According to one embodiment of the invention, the light alkyl (meth)acrylate is ethyl acrylate (EA), the heavy alcohol is 2-octanol, the (meth)acrylic ester is 2-octyl acrylate (2OCTA), and the dialkyl phthalate is diethyl phthalate.

According to one embodiment of the invention, the light alkyl (meth)acrylate is butyl acrylate (BuA), the heavy alcohol is 2-octanol, the (meth)acrylic ester is 2-octyl acrylate (2OCTA), and the dialkyl phthalate is dibutyl phthalate.

The dialkyl phthalate may be introduced as is into the heavy fraction at the cracking reactor, or introduced in solution in a solvent, or else in solution in one of the reagents of the process.

The dialkyl phthalate may be introduced at a concentration ranging from 0.001% to 1% by weight, especially from 0.01% to 5% by weight, preferably from 0.1% to 0.5% by weight into the heavy fraction to be treated.

The dialkyl phthalate has the advantage of acting both as antifouling agent and viscosity-reducing agent (fluxing agent) in the heat treatment step. The result thereof is a final residue having a suitable viscosity for being readily transportable by means of a pump, this viscosity generally being less than 200 cP, preferably less than 50 cP.

The heavy fraction contains virtually all of the catalyst used to carry out the transesterification reaction.

The heavy fraction to be treated may contain various polymerization inhibitors among which mention may be made of phenothiazine (PTZ), hydroquinone (HQ) and derivatives thereof such as hydroquinone methyl ether, 2,6-di-tert-butyl-4-methylphenol (BHT), N-oxyl compounds of 4-hydroxy-2,2,6,6-tetramethylpiperidinoxyl (4-OH-TEMPO) type and mixtures thereof in any proportions. It is possible to add an amount of polymerization inhibitor ranging from 500 to 5000 ppm before subjecting the heavy fraction to the heat treatment.

The heat treatment is carried out at a temperature ranging from 100° C. to 250° C., preferably from 150 to 200° C., making it possible to eliminate, by distillation, the valuable products initially present and the valuable products resulting from the thermal cracking of the Michael adducts.

The heat treatment is carried out without adding additional catalyst into the heavy fraction to be treated.

The heat treatment may be carried out in batch or continuous mode in a jacketed reactor or in a reboiler surmounted by a column which above all has the role of demister in order to limit the rise of the inhibitors.

The residence time is generally between 30 min and two hours.

It may be advantageous to only subject a portion of the heavy fraction to the heat treatment, and to recycle the other portion to the transesterification reaction.

According to this embodiment, the amount of fresh catalyst to be introduced into the transesterification reactor may be reduced down to 50% by weight, without observing an increase in the concentration of heavy compounds in the reactor.

From 5% to 50%, more particularly from 10% to 30% by weight of the heavy fraction are preferably recycled to the reaction, the remainder being subjected to the heat treatment.

In a preferred variant of the invention, prior to the heat treatment, the heavy fraction is conveyed over a film evaporator in order to recover and recycle the light compounds present in trace amounts.

According to this variant, it is also advantageous to only subject a portion of the bottom stream from the film evaporator to the heat treatment, and to recycle the other portion to the transesterification reaction.

From 5% to 50%, more particularly from 10% to 30% by weight of the bottom stream from the film evaporator are preferably recycled to the reaction, the remainder being subjected to the heat treatment.

At the end of the heat treatment, the valuable products, essentially the desired (meth)acrylic ester and the unreacted alcohol, are recovered in the form of a distillate, after distillation under nitrogen atmosphere or air depleted to 8 vol % of oxygen and under reduced pressure, for example from 10 to 50 mbar. The use of depleted air is preferred.

The valuable products recovered in this way are reclaimed by recycling them in the facility, at different steps of the process; either at the reaction or at the steps for purification of the crude reaction product.

Since the temperature of the medium remains greater than 60° C., the final residue is sufficiently fluid to be directly transportable by means of a pump.

The final residue is rich in transesterification catalyst and may advantageously be at least partially recycled to the step of reaction by transesterification.

From 5% to 50%, more particularly from 10% to 20% by weight of final residue are preferably recycled to the reaction, the remainder being finally eliminated by incineration.

Appended FIG. 1 illustrates a continuous process for producing ADAME by transesterification starting from EA and DMAE, in which steps (a) to (i) are more generally applicable to the production of (meth)acrylic esters by transesterification starting from light $C_1$-$C_4$ alkyl (meth) acrylates, and from heavy alcohols defined in the process according to the invention.

According to a first step (a), the transesterification reaction between EA and DMAE is carried out in the reactor 1 in the presence of a catalyst, preferentially tetraethyl titanate, and polymerization inhibitors. The reactor 1 is surmounted by a distillation column 2 which serves to eliminate the light alcohol formed (ethanol) as it is formed, and to thereby shift the reaction equilibrium towards the formation of ADAME.

The azeotropic fraction generated during the transesterification reaction is advantageously recycled to the unit for producing light alkyl (meth)acrylate (step (f)), since it does not contain any bothersome impurities liable to form (meth) acrylic by-products.

According to step (b) of the process, the reaction mixture is subjected to distillation on a distillation column (tailing column 3). At the top of the column 3, a stream 7 is recovered which has had virtually all the catalyst and polymerization inhibitors removed from it and which comprises the ADAME produced and light compounds with a minority fraction of Michael adducts and heavy products.

At the bottom of the column 3, a heavy fraction 4 is recovered, comprising the catalyst, the polymerization inhibitors, the Michael adducts and the heavy compounds such as oligomers and polymers with a minority fraction of ADAME and DMAE and traces of light compounds.

According to step (c) of the process, the stream 7 is subjected to purification which is carried out by means of the distillation column 8, the top stream 9 of which is recycled to the reaction, the bottom stream 10 being directed to a distillation column 11, making it possible to obtain purified ADAME 12 at the top and a stream 13 at the bottom which is rich in inhibitors and which is recycled to the stream of crude reaction mixture supplying the column 3.

According to step (d) of the process, the heavy fraction 4 originating from the bottom of the column 3, which especially contains the catalyst, is partially (stream 22) subjected to the process according to the invention for recovering valuable products (ADAME and DMAE) in the reactor 15, the other portion (stream 24) being able to be recycled to the reactor 1 (step (i) of the process).

At least one portion (stream 25) of the heavy fraction may be concentrated beforehand on a film evaporator 5 which makes it possible to separate the traces of light compounds which are then recycled to the feed of column 3. The heavy fraction 6 originating from the evaporator generally contains, by weight, approximately 1% to 20% of DMAE, 10% to 30% of ADAME, 10% to 40% of Michael adducts [DMAE-ADAME], the remainder essentially consisting of from 10% to 50% by weight of catalyst and polymerization inhibitors and other heavy by-products.

A portion of this stream 6 may be recycled to the reaction (stream 19) in order to reduce the feed of fresh catalyst.

A portion of the heavy fraction 6, with the light compounds removed from it, is conveyed into the reactor 15 (stream 23) after addition of a dialkyl phthalate 14 under the conditions indicated above.

As a variant, a portion of the heavy fraction 4 (stream 21) may be mixed with the bottom stream from the film evaporator, in order to at least partially be subjected to the heat treatment. In the absence or presence of film evaporator, a portion of the heavy fraction may be eliminated by incineration.

The reactor 15 may be of the jacketed type or reboiler type surmounted by a distillation column 17 of low efficacy (1 to 3 theoretical plates) which more accurately serves as demister.

In the reactor 15, the heavy fraction comprising the Michael adducts is subjected to thermal cracking making it possible to recover a stream 18 rich in DMAE and ADAME at the top of the column 17.

The thermal cracking carried out under the conditions according to the invention makes it possible to recover, by simple distillation, more than 80% by weight of the valuable products (ADAME and DMAE) contained in the fraction 6 originating from the evaporator 5, and to obtain a degree of cracking of the Michael adducts of more than 60 wt %, or even more than 70 wt %.

The stream 18 may be recycled, according to step (e) of the process, at the synthesis reactor 1, at the inlet of the topping column 3, or at the inlet of the column 8 for purification of the ADAME; a combination of these different modes of recycling is possible.

The final residues 16 at the outlet of the reactor 15, rich in catalyst and polymerization inhibitors, may be at least partially recycled into the synthesis reactor 1 (stream 20), the remainder being incinerated, in the final step (h).

It is understood that the process of the invention may comprise any combination of the different variants described.

The examples below illustrate the present invention without however limiting the scope thereof.

EXAMPLES

Unless indicated otherwise, the percentages are expressed as percentages by weight.
The following abbreviations are used;
EA: Ethyl acrylate
DMAE: N,N-dimethylaminoethanol
ADAME: N,N-dimethylaminoethyl acrylate
APA: Michael adduct resulting from the addition of DMAE onto ADAME: [DMAE-ADAME]
EPA: Michael adduct resulting from the addition of DMAE onto EA: [DMAE+EA]

Example 1 (Comparative)

300 g of a heavy residue originating from an ADAME synthesis starting from EA and DMAE are introduced into a mechanically stirred glass reactor, heated by means of an electrical heating mantle and surmounted by a Vigreux column with condenser, vacuum distillation receiver and collecting vessels.

The composition by weight of this residue is as follows:
DMAE: 15.8%-ADAME: 17.5%-APA: 22.3%-EPA: 2.5%-q.s. 100%: heavy products+catalyst+inhibitors. This residue does not contain methanol.

5000 ppm of the compound Nalco® EC3368A were added to the mixture, before heating the residue with stirring and nitrogen bubbling for 90 min at 180° C. under a working pressure of 50 mbar. The following were recovered:
Distillate: 150 g
Final residue: 132 g
The composition by weight of the distillate is:
DMAE: 22.3%
ADAME: 50.5%
APA: 11.66%
EA: 0.44%
Methanol: 95 ppm
Other heavy products: q.s. 100%

There is minimal fouling of the reactor, the final residue is viscous but does not solidify at room temperature.

Example 2 (According to the Invention)

Example 1 was reproduced, replacing the compound Nalco® EC3368A with diethyl phthalate from Sigma Aldrich.
The subsequent treatment is similar to example 1.
The following were recovered:
Distillate: 155 g
Final residue: 133 g
The composition by weight of the distillate is:
DMAE: 23.7%
ADAME: 57.2%
APA: 6.52%
EA: 0.84%
Methanol: 0 ppm
Other heavy products: q.s. 100%

There is minimal fouling of the reactor, the final residue is viscous but does not solidify at room temperature. Moreover, the use of diethyl phthalate as fluxing/dispersing agent made it possible to avoid the formation of methanol in the distillate, which can thus be recycled without generating impurities in the process for synthesizing ADAME.

Example 3 (Continuous, Comparative)

A heavy fraction from an ADAME synthesis was introduced by means of a membrane pump into a glass reactor consisting of a thermosiphon reboiler. The feed flow rate is regulated by measuring the weight of residue in the tank. The reboiler is heated by means of a jacketed oil bath with a power of 160 W in order to minimize the skin temperature. The assembly is lagged and the heating temperature is adjusted to have the required temperature in the reboiler. At the top of the reboiler, a column element equipped with a multiknit element serving as demister has been added.

The bottom fraction was recovered by overflowing into the reboiler then taken up by a pump to be directed towards a receiver.

The operations were carried out under reduced pressure (50 mbar) and with nitrogen bubbling.

The composition by weight of the heavy fraction introduced is as follows:
DMAE: 5%
ADAME: 21.6%
APA: 35.7%
EA: 0.4%
q.s. 100%: heavy products+catalyst+inhibitors.
The heavy fraction does not contain methanol.
5000 ppm of the compound Nalco® EC3368A were added to the mixture.
The operating parameters of the micropilot plant are as follows:
Feed flow rate: 110 g/h
Residence time: 90 min
Pressure: 50 mbar
Reboiler temperature: 180° C.

After one hour of reaction, 51 g of distillate and 59 g of final residue were recovered.
The composition by weight of the distillate is:
DMAE: 23.3%
ADAME: 66.1%
APA: 0%
EA: 2.9%
Methanol: 104 ppm
The composition by weight of the residue is:
DMAE: 13.2%
ADAME: 2.7%

APA: 29.9%
EA: 0.04%
Absence of methanol.
Heavy products+catalyst+inhibitors: q.s. 100%
The weight balances from this test are as follows:
ADAME: from 23.8 g present in the free state in the heavy fraction, 33.7 g are recovered, a portion of which originates from the thermal cracking of the APA.
DMAE: from 5.5 g present in the free state in the heavy fraction, 11.8 g are recovered, a portion of which originates from the thermal cracking of the APA.
APA: from 39.3 g present in the heavy fraction, there is only 17.6 g remaining after thermal cracking of the APA.

The degree of cracking of the APA, expressed as the weight of APA which has disappeared by cracking relative to the weight present, is of the order of 55%.

The reactor is perfectly clean (no attachment of solids) and the final residue is perfectly fluid under hot conditions.

However, a not inconsiderable amount of ethanol is present in the distillate, which leads to the presence of a bothersome impurity during the recycling of the distillate in the synthesis process.

Example 4 (Continuous, According to the Invention)

Example 3 was reproduced with a heavy fraction of the following composition:
DMAE: 10.3%
ADAME: 15.3%
APA: 22.1%
EA: 0.08%
Absence of methanol.
q.s. 100%: heavy products+catalyst+inhibitors.

The compound Nalco® EC3368A was replaced by diethyl phthalate (5000 ppm).

The operating parameters of the micropilot plant are as follows:
Feed flow rate: 200 g/h
Residence time: 90 min
Reboiler temperature: 180° C.

After one hour of reaction, 125 g of distillate and 75 g of final residue were recovered.

The composition by weight of the distillate is:
DMAE: 19.9%
ADAME: 68.2%
APA: 0%
EA: 1.46%
Absence of methanol.

The composition by weight of the residue is:
DMAE: 8.9%
ADAME: 0.9%
APA: 8.6%
EA: 0.005%
Absence of methanol.
q.s. 100%: heavy products+catalyst+inhibitors.
Weight Balance:
ADAME: from 30.6 g present in the free state in the heavy fraction, 85.25 g are recovered, a portion of which originates from the thermal cracking of the APA.
DMAE: from 20.6 g present in the free state in the heavy fraction, 24.8 g are recovered, a portion of which originates from the thermal cracking of the APA.
APA: from 44.2 g present in the heavy fraction, there is only 8.7 g remaining after thermal cracking of the APA.

Under these conditions, the degree of cracking of the APA is of the order of 80%, the reactor is perfectly clean (no attachment of solids) and the final residue is perfectly fluid under hot conditions. Moreover, the distillate does not contain any methanol, which makes it possible to advantageously return this fraction to a step of the synthesis and/or purification process.

The use of the diethyl phthalate made it possible both to avoid returning methanol to the distillate fraction but also to improve the degree of cracking of the heavy by-products.

Example 5 (Continuous, According to the Invention)

Example 4 was reproduced with the following conditions:
The composition by weight of the heavy fraction introduced is as follows:
DMAE: 16%-ADAME: 14%-APA: 24%-q.s. 100%: heavy products+catalyst+inhibitors.
5000 ppm of diethyl phthalate were added.

The operating parameters of the micropilot plant are as follows:
Feed flow rate: 200 g/h
Residence time: 90 min
Pressure: 50 mbar
Reboiler temperature: 180° C.
Degree of depletion: 50%

After one hour of reaction, 100 g of distillate and 100 g of final residue were recovered.

The composition by weight of the distillate is:
DMAE: 23.1%
ADAME: 60.5%
APA: 0.06%
EA: 2.5%
EPA: 0%

The composition by weight of the residue is:
DMAE: 14.5%
ADAME: 1.7%
APA: 9.6%
Heavy products+catalyst+inhibitors: q.s. 100%

The weight balances demonstrate the reclamation of the ADAME and the DMAE recovered during the process according to the invention:
ADAME: from 28.9 g present in the free state in the heavy fraction, 61.1 g are recovered, a portion of which originates from the thermal cracking of the APA.
DMAE: from 33.3 g present in the free state in the heavy fraction, 23.3 g are recovered, a portion of which originates from the thermal cracking of the APA.
APA: from 48.4 g present in the heavy fraction, there is only 9.8 g remaining after thermal cracking of the APA.
The degree of cracking is 79.8%.

The reactor is clean and the final residue is fluid under hot conditions.

Example 6: Effect of Recycling the Catalyst Present in the Bottom Stream from the Film Evaporator DMAE (2.73 mol), EA (4.7 mol, 1.6 molar eq.), and 21.84 mmol of $Ti(OEt)_4$ as transesterification catalyst are introduced into a 1 liter glass reactor mechanically heated by means of a jacket.

According to the tests, the catalyst used is an 85/15 solution by weight of pure $Ti(OEt)_4$ in DMAE, or a mixture of this solution with $Ti(OEt)_4$ resulting from a stream of heavy products originating from the bottom of a film evaporator from an industrial ADAME unit.

The reaction medium is then heated at 110° C. for 3 h, the EA/EtOH azeotropic mixture is withdrawn to shift the equilibrium.

The crude reaction product is then analyzed to calculate the yield. Analysis of the crude product is carried out by gas chromatography.

The yield of ADAME formed under these conditions is determined from the number of moles of ADAME produced relative to the number of moles of DMAE introduced.

TABLE 1

| Test | $Ti(OEt)_4$ catalyst in DMAE, mmoles of $Ti(OEt)_4$ | $Ti(OEt)_4$ from recycling, mmoles of $Ti(OEt)_4$ | Yield of ADAME, % |
|---|---|---|---|
| 1 | 21.84 | 0 | 77 |
| 2 | 17.47 | 0 | 71 |
| 3 | 10.92 | 0 | 57 |
| 4 | 17.47 | 4.37 | 76 |
| 5 | 10.92 | 10.92 | 76 |

The results of the tests carried out, collated in table I above, show that recycling the heavy fraction separated on a film evaporator makes it possible to save almost 50% by weight of esterification catalyst, with equivalent production.

The invention claimed is:

1. A process for recovering unreacted reagents and (meth)acrylic ester products from a heavy (meth)acrylic fraction generated during production of a (meth)acrylic ester by a continuous transesterification reaction of a light $C_1$-$C_4$ alkyl (meth)acrylate with a heavy alcohol in the presence of a catalyst, the heavy fraction comprising at least unreacted reagents and (meth)acrylic ester products and Michael adducts resulting from addition reactions on the (meth)acrylic double bonds and also the catalyst, said process comprising heat treating said heavy fraction at a temperature sufficient to crack the Michael adducts into their constituent components, recovering unreacted reagents and (meth)acrylic ester products in the form of a distillate, and eliminating fluid final residue by means of a pump, wherein the heat treatment is carried out in the presence of at least one antifoulant and viscosity reducing agent which is a dialkyl phthalate, the alkyl chain of which corresponds to that of the light alkyl (meth)acrylate.

2. The process as claimed in claim 1, wherein the light alkyl (meth)acrylate is methyl acrylate and the dialkyl phthalate is dimethyl phthalate.

3. The process as claimed in claim 1, wherein the light alkyl (meth)acrylate is ethyl acrylate and the dialkyl phthalate is diethyl phthalate.

4. The process as claimed in claim 1, wherein the light alkyl (meth)acrylate is butyl acrylate and the dialkyl phthalate is dibutyl phthalate.

5. The process as claimed in claim 1 wherein the dialkyl phthalate is added at a concentration ranging from 0.001% to 1% by weight into the heavy fraction to be treated.

6. The process as Claimed in claim 1 wherein the heavy alcohol is an aminoalcohol of formula (II):

HO-A-N(R'$_2$) (R'$_3$)    (II)

in which
A is a linear or branched $C_1$-$C_5$ alkylene radical,
R'$_2$ and R'$_3$, which are identical to or different from one another, each represent a $C_1$-$C_4$ alkyl radical.

7. The process as claimed in claim 6, wherein the heavy alcohol is N,N-dimethylaminoethanol.

8. The process as claimed in claim 1 wherein the heavy alcohol is an alcohol of formula $R_2OH$, in which $R_2$ represents a linear or branched $C_5$-$C_{12}$ alkyl chain.

9. The process as claimed in claim 1 wherein at least a portion of the heavy fraction is recycled to the transesterification reaction, the other portion being subjected to said heat treatment.

10. The process as claimed in claim 1 wherein the heavy fraction is subjected beforehand to purification by passage over a film evaporator, at least a portion of the bottom stream from the film evaporator being recycled to the transesterification reaction, the other portion being subjected to said heat treatment.

11. process for producing a (meth)acrylic ester by a continuous transesterification reaction between a light $C_1$-$C_4$ alkyl (meth)acrylate and a heavy alcohol, said process comprising at least the following steps:
 a) subjecting a reaction mixture, comprising a light alkyl (meth)acrylate, a heavy alcohol, a transesterification catalyst and at least one polymerization inhibitor, to transesterification conditions in order to form i) a mixture of products comprising (meth)acrylic ester, unreacted light alkyl (meth)acrylate, and heavy alcohol, catalyst, polymerization inhibitors, Michael adducts resulting from addition reactions onto the (meth)acrylic double bonds, and heavy compounds; and ii) an azeotropic mixture of light alkyl (meth)acrylate/free light alcohol;
 b) distilling the mixture i) of products in order to recover, at the top, a stream comprising (meth)acrylic ester and light products, a minority fraction of Michael adducts, heavy products and polymerization inhibitors, and which is substantially free of catalyst, and in order to leave, at the bottom, a heavy fraction comprising catalyst, polymerization inhibitors, Michael adducts and heavy compounds, with a minority fraction of (meth)acrylic ester and heavy alcohol and traces of light products;
 c) purifying the top stream to obtain purified (meth)acrylic ester;
 d) subjecting at least a portion of the heavy fraction to a process for recovering unreacted reagents and (meth)acrylic ester products in the form of a distillate as defined in claim 1;
 e) recycling at least a portion of said distillate into at least one step chosen from the group consisting of step a) of reaction, step b) of distillation and step c) of purification;
 f) optionally recycling the azeotropic mixture ii) formed in step a), to the light alkyl (meth)acrylate production unit;
 g) optionally recycling at least a portion of the fluid final residue resulting from step d), to step a) of reaction;
 h) incinerating the fluid final residue resulting from step d);
 i) optionally recycling a portion of the heavy fraction to step a) of reaction.

12. The process as claimed in claim 11, Wherein said heavy fraction is subjected beforehand to purification by passage over a film evaporator before step d).

13. The process as claimed in claim 12, wherein a portion of the bottom stream from the film evaporator is recycled to step a) of reaction.

14. The process as claimed in claim 11 wherein step of purification c) is carried out using two distillation columns in series and at least a portion of the distillate resulting from step d) is recycled to the top of the first purification column.

15. The process as claimed in claim 11 wherein (meth) acrylic ester is N,N-dimethylaminoethyl acrylate resulting from the transesterification reaction between N,N-dimethylaminoethanol and ethyl acrylate, and step d) is carried out in the presence of diethyl phthalate.

* * * * *